(12) United States Patent
Manohar et al.

(10) Patent No.: US 10,365,272 B2
(45) Date of Patent: Jul. 30, 2019

(54) HIGHLY SENSITIVE IMMUNOASSAY FOR RAPID QUANTIFICATION OF MENINGOCOCCAL CAPSULAR POLYSACCHARIDE ANTIGENS

(71) Applicant: SERUM INSTITUTE OF INDIA Private Limited, Maharashtra (IN)

(72) Inventors: Kale Sameer Manohar, Maharashtra (IN); Sharma Pankaj Keshav, Maharashtra (IN); Gairola Sunil Jagdishprasad, Maharashtra (IN)

(73) Assignee: SERUM INSTITUTE OF INDIA PRIVATE LIMITED, Maharashtra (IN)

( * ) Notice: Subject to any disclaimer, the term of this patent is extended or adjusted under 35 U.S.C. 154(b) by 0 days.

(21) Appl. No.: 14/808,352

(22) Filed: Jul. 24, 2015

(65) Prior Publication Data
US 2016/0025719 A1 Jan. 28, 2016

(30) Foreign Application Priority Data
Jul. 25, 2014 (IN) .......................... 2414/MUM/2014

(51) Int. Cl.
*G01N 33/543* (2006.01)
*G01N 33/569* (2006.01)

(52) U.S. Cl.
CPC . *G01N 33/54306* (2013.01); *G01N 33/56911* (2013.01); *G01N 2333/22* (2013.01); *G01N 2400/00* (2013.01)

(58) Field of Classification Search
None
See application file for complete search history.

(56) References Cited

U.S. PATENT DOCUMENTS

| | | | | |
|---|---|---|---|---|
| 5,817,320 A * | 10/1998 | Stone | ...................... | A01N 37/18 424/278.1 |
| 2004/0006128 A1* | 1/2004 | Bibbs | ................... | A61K 31/353 514/456 |
| 2006/0251670 A1* | 11/2006 | Comanducci | ........ | A61K 39/095 424/190.1 |
| 2009/0068200 A1* | 3/2009 | Choquet-Kastylevsky | ................. | G01N 33/57415 424/172.1 |

FOREIGN PATENT DOCUMENTS

WO WO 2013/174832 * 11/2013
WO WO 2014/080423 * 5/2014

OTHER PUBLICATIONS

Su et al. Journal of Argricultural and Food Chemistry, 2013, 61, 10823-10833.*
Kircanski et al. Journal of Veterinary Diagnostic Investigation. Sep. 2012 vol. 24 No. 5 895-902.*
Annex 2: Recommendations to Assure the Quality, Safety and Efficacy of Group A meningococcal Conjugate Vaccines. Aug. 11, 2011. Retrieved on May 5, 2016 at: http://www.who.int/biologicals/vaccines/Annex_2_WHO_TRS_962.pdf.*
ELISA technical guide. Thermo Scientific. 2010.*
Biolegend Sandwich ELISA protocol Mar. 1, 2007.*
Reyes et al. Journal of Immunological Methods 407 (2014) 58-62.*
Chazot et al. Methods in Molecular Biology, vol. 128: NMDA Receptor Protocols. Edited by: M. Li. Humana Press Inc., Totowa NJ.*
Leenaars et al. ILAR J (2005) 46 (3): 269-279 Jul. 1, 2005.*
Teillaud et al. Science Nov. 18, 1983;222(4625):721-6.*
In re Wands 858 F.2d 731 (Fed. Circ. 1988), 9 pages.*
Ferrara et al. mAbs, 7:1, 32-41, 2015.*
Torres et al. Trends in Immunolgoy vol. 29, No. 2 p. 91-97, 2007.*
Goel et al. J Immunol, 2004, 173 (12) 7358-7367 Dec. 15, 2004.*

* cited by examiner

*Primary Examiner* — Oluwatosin A Ogunbiyi
(74) *Attorney, Agent, or Firm* — Brooks Kushman P.C.

(57) ABSTRACT

The present disclosure relates to the field of immunoassays for Gram negative bacteria, in particular *N. meningitidis*. The disclosure provides a simple and affordable immunoassay to quantitate polysaccharides in meningococcal vaccines for the evaluation of antigen content and lot-to-lot manufacturing consistency. The inventors have found a Sandwich ELISA that can be applicable for the quantitation and identification of *N. meningitidis* serogroup X polysaccharide in a multivalent meningococcal polysaccharide-protein conjugate vaccine as well as in a multivalent meningococcal plain polysaccharide vaccine. Said assay employs a polyclonal antibody as capture antibody and a novel monoclonal antibody against serogroup X polysaccharide as detection antibody. Further the assay is rapid, robust and reproducible.

19 Claims, 11 Drawing Sheets

HIGHLY SENSITIVE IMMUNOASSAY FOR RAPID QUANTIFICATION OF MENINGOCOCCAL CAPSULAR POLYSACCHARIDE ANTIGENS

CROSS-REFERENCE TO RELATED APPLICATIONS

This application claims priority benefits under 35 U.S.C. § 119(a)-(d) to Indian patent application number 2414/MUM/2014, filed Jul. 25, 2014, which is incorporated by reference in its entirety.

BRIEF DESCRIPTION

The capsular saccharides of bacteria have been used for many years in vaccines against capsulated bacteria. As saccharides are T-independent antigens, however, they are poorly immunogenic. Conjugation to a carrier can convert T-independent antigens into T-dependent antigens, thereby enhancing memory responses and allowing protective immunity to develop. The most effective saccharide vaccines are therefore based on glycoconjugates, and the prototype conjugate vaccine was against *Haemophilus influenzae* type b ('Hib').

Based on the organism's capsular polysaccharide, twelve serogroups of *N. meningitidis* have been identified (A, B, C, H, I, K, L, 29E, W135, X, Y and Z). Group A is the pathogen most often implicated in epidemic disease in sub-Saharan Africa. Serogroups B and C are responsible for the vast majority of cases in USA and in most developed countries. Serogroups W135 and Y are responsible for the remaining cases in USA and developed countries. A tetravalent vaccine of capsular polysaccharides from serogroups A, C, Y and W135 has been known for many years. Although effective in adolescents and adults, it induces a poor immune response and short duration of protection and cannot be used in infants because polysaccharides are T cell-independent antigens that induce a weak immune response which cannot be boosted. The polysaccharides in this vaccine are not conjugated. Conjugate vaccines against serogroups C and A have been approved for human use, and include Menjugate™, Meningitec™, NeisVac-C™ and MenAfriVac™. Mixtures of conjugates from serogroups A+C are known and mixtures of conjugates from serogroups A+C+W135+Y have been reported.

X serogroup has been associated with a number of outbreaks of meningococcal disease, e.g. in sub-Saharan Africa and China. Serogroup X is known to have a significantly higher attack rate than serogroup A among children below 5 years of age. Although the need for a vaccine against this serogroup has been recognized for many years, no effective vaccine has been developed. Gunnstein Norheim discusses that at present vaccine against serogroup X is not available and that next generation affordable vaccines should target most prevalent serogroups: A, W-135, X. Refer "Preventing the emerging serogroup X meningococcal disease in the African Meningitis Belt" Oxford Vaccine Group, 2011. Accordingly, there remains a need for conjugates of serogroup X capsular polysaccharides. Moreover, there remains a need for conjugates that can be used for vaccination against diseases caused by this serogroup.

The structure of the group X capsular polysaccharide consists of N-acetylglucosamine-4-phosphate residues held together by α 1-4 phosphodiester bonds without O-acetyl groups. Refer Bundle et al. (1974) J Biol Chem 249:2275-81. Based on the similarity between their structures, a biosynthetic relationship between MenA and MenX capsular polysaccharides has been postulated. MenA capsular polysaccharide tends to hydrolyse significantly in aqueous solution. This instability is thought to be caused by the presence of a phosphodiester linkage involving the anomeric position and of the N-Acetyl group in position 2 of mannosamine, which can assist departure of a phosphomonoester group. Another possibility is that the hydroxyl groups at position 4 of the N-acetylmannosamine subunits interact with the phosphodiester groups facilitating hydrolysis via an internal participation mechanism, as seen in the capsular polysaccharide of type 6A pneumococcus and *Haemophilus influenzae* type b. The similarity in the structures of the MenX and MenA capsular polysaccharides, particularly their common anomeric phosphodiester linkage, means that the MenX polysaccharide may suffer from similar stability problems when in aqueous solution.

Most meningococcal vaccines are monovalent or multivalent mixtures of either polysaccharides or polysaccharides conjugated to carrier proteins. Quantitative determination of the individual polysaccharide components in multivalent meningococcal vaccines is an important step in manufacturing and regulatory control. Refer Cook M C et al "Quantitation of serogroups in multivalent polysaccharide-based meningococcal vaccines: optimization of hydrolysis conditions and chromatographic methods" Vaccine 2013, 31:3702-3711.

Several methods for individual quantitation of meningococcal polysaccharides have been described. Determination of total phosphorus content has been employed for measurement of MenA and MenX, while sialic acid content can be used for MenC, MenW, and MenY. High performance anion exchange chromatography with pulsed amperometric detection (HPAEC-PAD) has been used for the quantitation of polysaccharides in multivalent meningococcal CP-based vaccines. Refer Chen P S et al "Microdetermination of phosphorus" Anal Chem 1956, 28:1756-1760; Svennerholm L et al "Quantitative estimation of sialic acids. II. A colorimetric resorcinol-hydrochloric acid method" Biochim Biophys Acta 1957, 24:604-611; Gibeault S et al "Serogroup quantitation of multivalent polysaccharide and polysaccharide-conjugate meningococcal vaccines from China" Biologicals 2013, 41:261-268; Lamb D H et al "Determination of meningococcal polysaccharides by capillary zone electrophoresis". Anal Biochem 2005, 338:263-269; Ricci S et al "Development of a new method for the quantitative analysis of the extracellular polysaccharide of *Neisseria meningitidis* serogroup A by use of high-performance anion-exchange chromatography with pulsed-amperometric detection" Vaccine 2001, 19:1989-1997 and Lei Q et al "Quantification of free polysaccharide in meningococcal polysaccharide-diphtheria toxoid conjugate vaccines" Developments in biologicals 2000, 103:259.

Accordingly Phosphorus and sialic acid assays can't be used in multivalent meningococcal vaccines (trivalent, tetravalent, pentavalent) because phosphorus is present in MenA and MenX CP and it becomes difficult to interpret contribution of individual phosphorus from serotype A or X. Further quantitation of polysaccharides in meningococcal multivalent vaccines using CZE method has not been fully evaluated.

Further, use of (High performance anion exchange chromatography with pulse amperometric detector i.e. HPAEC PAD) has been reported for MenC, MenW and MenY Capsular polysaccharide. However, HPAEC PAD method requires prior conversion of polysaccharide to Monomeric units by acid digestion and the presence of high concentration of saccharide excipient such as sucrose (Glucose+ fructose) may interfere with the determination of polysaccharide content of different meningococcal serogroup. Also, Men Y polysaccharide contain N-Acetyl Neuraminic acid (NANA)+Glucose as a monomeric unit and Men W contains N-Acetyl Neuraminic acid+Galactose as a monomeric unit. Digestion of sample which is must required step in HPAEC-PAD analysis breaks saccharide and yields NANA and glucose/Galactose. Glucose is also present in excipient which interferes in the assay. Hence HPAEC-PAD method is difficult to perform and adds considerable time and expense to the procedure. Further the use of strong acids, often at elevated temperature, represents a potential safety concern for laboratory staff and has a cost associated with material disposal.

The development of a vaccine against MenX requires a method for polysaccharide quantification that can be used as an in-process assay and/or for the characterization of the final vaccine. The presence of phosphate groups in the MenX capsular polysaccharide means that the polysaccharide can be quantified by a colorimetric method that measures total phosphorus content. However, this method lacks selectivity and therefore would not be suitable for certain in-process applications, e.g. for the analysis of polysaccharide in phosphate buffers or in the presence of phosphate-containing impurities. A more selective method would be NMR, which has been proposed already for MenX polysaccharide quantification. However, this approach requires pure samples and a large amount of material. Xie et al. demonstrates an alternative approach, where the MenX polysaccharide is quantified by HPAEC-PAD, which is more sensitive than NMR and more selective than measuring phosphate content wherein MenX polysaccharide was quantified by hydrolysing the sample to make glucosamine, and comparing the amount of glucosamine released against a calibration curve derived from an N-acetyl-glucosamine-6-phosphate quantitative standard. Refer Vaccine 2012 (30) 5812-5582. However, glucosamine may be present because of contamination, leading to inaccurate results.

Accordingly, HPAEC-PAD and chemical methods like Chen or Ames have following inherent drawbacks i) interference of excipients and ii) inability to accurately quantify individual serotype polysaccharide in a multivalent composition. Thus there is an unmet need for an alternative or improved method for assaying individual polysaccharides (ACWY), particularly for assaying the MenX polysaccharide in a multivalent composition.

Present inventors have surprisingly found an immunoassay that could be particularly employed for assaying a sample suspected to contain serogroup X capsular polysaccharide or serogroup X capsular polysaccharide-protein conjugate that overcomes the setbacks of already existing quantification methods.

SUMMARY

The disclosure relates to a novel Sandwich ELISA for Men X polysaccharide quantification in monovalent or multivalent polysaccharide-protein conjugate vaccine/plain polysaccharide samples that overcomes limitations of HPAEC-PAD and other chemical methods routinely utilized for polysaccharide quantification.

An object of the disclosure is to provide a Sandwich ELISA for Men X polysaccharide quantification in multivalent polysaccharide-protein conjugate vaccine/plain polysaccharide vaccine samples having following novel features:

1) A robust and affordable assay to quantitate polysaccharides in meningococcal vaccines that is essential for the evaluation of antigen content and lot-to-lot consistency of manufacture.
2) Assay applicable for the quantitation of serogroup X polysaccharide-protein conjugate in a multivalent meningococcal polysaccharide-protein conjugate vaccine and quantitation of serogroup X polysaccharide in a multivalent plain polysaccharide vaccine.
3) Overcomes the lack of ability of the previously reported chemical assays to quantitate due to presence of similar backbone polysaccharide conjugate in polyvalent vaccine by applying antigen antibody binding concept.
4) Assay is devoid of interference occurring due to the presence of excipients like sucrose and sodium citrate that has been reported previously for chemical and chromatography based assays.
5) Instant Sandwich ELISA utilizes a Polyclonal antibody as Capture antibody and Monoclonal antibody as Detection antibody wherein the capture and detection antibodies recognize two different non-overlapping epitopes thereby ensuring that when the antigen binds to the capture antibody, the epitope conformation recognized by the detection antibody is not obscured or altered. Further employing Polyclonal antibody can quantify signal from target antigen with changed or low concentration and also indicate cross-reactivity. Whereas previously reported methods utilize monoclonal antibody as capture as well as detection antibody.
6) The monoclonal antibodies against serogroup X polysaccharide used as detection antibody have been developed in-house and do not show any cross-reactivity for serogroups A C W & Y.
7) Capture antibody and binding antibody both being from different sources make said assay rugged.
8) Method shows LOD of 0.4 ng/ml and LOQ of 1.6 ng/ml for *N. meningitidis* Serogroup X.
9) Assay requires total duration of about 1 day whereas previously reported methods require 2 days.

Other objects and characteristics of the present disclosure will become apparent from the following detailed description.

DETAILED DESCRIPTION

As required, detailed embodiments are disclosed herein; however, it is to be understood that the disclosed embodiments are merely exemplary and that various and alternative forms are possible. Therefore, specific structural and functional details disclosed herein are not to be interpreted as limiting, but merely as a representative basis for teaching one skilled in the art to variously employ the present disclosure.

The present disclosure relates to a Sandwich ELISA for Men X polysaccharide quantification in multivalent polysaccharide-protein conjugate vaccine/plain polysaccharide vaccine samples comprising of:

1. Coating of Immunoplates by serogroup specific antiserum (Men A, C, Y, W & X). (Dilution is 1:5000 to 1:15000).
2. Incubation at a temperature between 30 to 40° C. for a duration of about 1 to 2 hour.
3. Washing of Immunoplates for 3 to 5 times by wash buffer: WFI+0.05% Tween 20).
4. Addition of blocking buffer containing Phosphate buffer saline, 2 to 7% FBS and 0.05% Tween 20.
5. Incubation at a temperature between 30 to 40° C. for a duration of about 1 to 2 hours.
6. Washing of Immunoplates for 3 to 5 times with wash buffer.
7. Addition of appropriately serially diluted polyvalent (Pentavalent/Quadrivalent) sample and standard.
8. Incubation at a temperature between 30 to 40° C. for a duration of about 1 to 2 hours.
9. Washing of Immunoplates for 3 to 5 times with wash buffer.
10. Addition of detection antibody solutions (Monoclonal Antibodies: 1:3000 to 1:10000).
11. Incubation at a temperature between 30 to 40° C. for a duration of about 1 to 2 hours.
12. Washing of Immunoplates for 3 to 5 times with wash buffer.
13. Addition of a secondary antibody preferably HRP-Conjugate antibody (Dilution is 1:5000 to 1:15000).
14. Incubation at a temperature between 30 to 40° C. for a duration of about 1 to 2 hours.
15. Addition of 100 µL substrate (TMB) in all the wells.
16. Incubation at RT for 15 to 30 minutes.
17. Final addition of 100 µL 2 N Sulphuric acid.
18. Reading the OD at 450 nm with reference at 630 nm.

A method for the detection and/or quantification of *N. meningitidis* serogroup X capsular polysaccharide in a sample is provided. The method includes providing a solid support coated with polyclonal antibody; providing a sample; applying the sample to the polyclonal antibody coated solid support; removing unbound sample; providing monoclonal antibody; applying the monoclonal antibody to the solid support; removing unbound monoclonal antibody; applying labeled secondary antibody; and detecting the label. The capture polyclonal antibody and detection monoclonal antibody recognize two distinct non-overlapping epitopes of *N. meningitidis* Serogroup X capsular polysaccharide.

An important aspect of instant disclosure is that said sample can be lyophilized or liquid. Preferably, i) lyophilized sample can be resuspended in phosphate buffer saline having pH 7.2±0.2 comprising of 75-140 mM KCl followed by further dilution and ii) liquid sample can directly be diluted with phosphate buffer saline having pH 7.2±0.2 comprising of 75-140 mM KCl.

A second embodiment of the instant disclosure is that said Sandwich ELISA does not show any interference due to presence of excipients like sucrose and glucose.

A third embodiment of the instant disclosure is that said detection monoclonal antibody against serogroup X 8210 shows no cross-reactivity with A, C, W, Y.

A first aspect of the third embodiment The accuracy of the Sandwich ELISA for quantifying *N. meningitidis* group X in a pentavalent conjugate vaccine (A-TT, X-TT, C-CRM197, W-CRM197, Y-CRM197) is about 100%.

A second aspect of the third embodiment of the instant disclosure is that said assay shows LOD of about 0.4 ng/ml and LOQ of about 1.6 ng/ml for serogroup X polysaccharide.

A fourth embodiment of the instant disclosure is that said solid support can be selected from PVC, polystyrene, agarose and sepharose most preferably polystyrene wherein support may be formed as a microtitration plate, tube or bead.

An object of the instant disclosure is that the microtitration plates are activated immunoassay plates.

A fifth embodiment of present disclosure is that said capture antibody is a Rabbit Polyclonal antibody or antiserum against *N. meningitidis* serogroup polysaccharides selected from but not limited to A C W Y and X.

A sixth embodiment of present disclosure is that said detection antibody is a Mouse Monoclonal antibody against *N. meningitidis* serogroup polysaccharides selected from but not limited to A C W Y and X.

A further embodiment of the present disclosure is that preparation of said detection monoclonal antibody against serogroup X 8210 can comprise of following steps:

1. Obtaining splenocytes from mice immunized with Men X conjugate.
2. Fusing splenocytes with SP2/O cells (mouse myeloma cells)
3. Selecting fused cells using Hypoxanthine Aminopterin Thymidine medium.
4. Screening supernatant of fused cells for presence of anti-Men X antibody by using bead based assay and rate nephelometry
5. Making limiting dilution of positive clones.
6. Propagating single anti-Men X antibody secreting clone to 6 well plate.
7. Subjecting clone to a second limiting dilution.
8. Selecting Anti-Men X antibody secreting clone by bead based assay.
9. Propagating selected clone to 2 Liters for production of Anti-Men X Monoclonal antibody. Purifying monoclonal antibody by protein A chromatography.

A still further object of the instant disclosure is that
i) preferred dilution of polyclonal capture antibody can be between 1:5000 to 1:15000 in carbonate buffer, pH 9.6.
ii) preferred dilution of the secondary monoclonal antibody can be between 1:3000 to 1:10000 in PBS, pH 7.2; and
iii preferred dilution of the antibody to the secondary antibody (preferably HRP-Conjugate antibody) can be between 1:5000 to 1:15000 in PBS, pH 7.2.

Yet another aspect of the instant disclosure is that blocking buffer can comprise of Phosphate buffered saline pH 7.2, 2 to 7% FBS and 0.05% Tween 20.

The labelled secondary antibody preferably HRP-Conjugate antibody of present disclosure can be labeled directly wherein direct labels typically include enzyme labels, fluorescent labels, radioactive labels and biotin; preferably enzyme labeled.

The enzymes used for labeling can either be a single enzyme, an oligomeric form of the enzyme, or an enzyme/antienzyme complex may be used.

Typically the label can be an enzyme selected from alkaline phosphatase, horse radish peroxidase, β-galactosidase and urease; a radioisotope selected from 125 I and 131 I; a fluorescent label selected from a fluorochrome, FITC and TRITC, or biotin; preferably horse radish peroxidase (HRP).

EXAMPLES

In view of the many possible embodiments to which the principles of the disclosure may be applied, it should be recognized that the illustrated embodiments are only preferred examples of the disclosure and should not be taken as limiting the scope of the disclosure.

Example 1

Total Phosphorus Estimation in Multivalent Vaccine by Chen Method or Ames Method

TABLE 1

| Product | Dose | Batch No. | Total Phosphorus (µg/mL) |
|---|---|---|---|
| Meningococcal ACYWX Polysaccharide Conjugate vaccine | 1 Dose | 234E4001 | 0.805 |
| | 5 Dose | 235E4001 | 3.883 |
| | 1 Dose | 234E4002 | 0.829 |
| | 5 Dose | 235E4002 | 4.683 |
| | 1 Dose | 234E5001 | 0.904 |
| | 5 Dose | 235E5001 | 4.740 |

Thus it was found that individual polysaccharide concentration for Men A and Men X cannot be calculated by chemical methods like chen method or Ames method

Example 2

Preparation of MenX-TT Conjugate
Polysaccharide Preparation

MenX-TT conjugate was prepared by cyanylation and carbodiimide chemistry. The native polysaccharide was size-reduced by mechanical means. The size-reduced PS (120-150 kD on SEC-HPLC) was diafiltered & concentrated on 10 kD cuttoff membrane. To 20 mg/ml PS, freshly prepared solution of CPPT (also known as CPPT dissolved 114 mg/ml in acetonitrile) was added and the pH was shifted to 9.5 with NaOH solution and incubated for 2-4 min. Adipic acid dihydrazide (ADH) was dissolved 100 mg/ml in water and added to the PS solution. The reaction was stirred for 3 hrs at 25° C. The reaction was quenched by addition of excess glycine solution. The reaction mixture was diafiltered in MES buffer to remove residuals and unreacted components. The sample was stored at 2-8° C. until use. The PS content was measured by phosphorous assay and extent of derivatization was measured by TNBS assay.

Carrier Protein (TT) Preparation:

The carrier Protein preparation process was similar as described above.

Conjugation of Men X to TT:

The ADH-derivatized PS, purified TT and EDAC (1-ethyl-3-(3-dimethyl-aminopropyl) carbodiimide) were mixed in a ratio of 1:1.5:0.7 by weight under stirring condition. The reaction progress was monitored on HPLC. The reaction was quenched after 3 hrs by raising pH with 10 mM PB+EDTA pH 8.0 buffer.

Conjugate Purification:

The conjugate was purified on 300 kD cut off membrane by passing 30 volumes of 100 mM PBS and followed by 30 volume 10 mM Tris pH 7.2. The purified bulk conjugate was analyzed for total and unbound (free) PS, total and protein and residual 4-PPY in the conjugate bulk.

TABLE 2

| Test Sample | Total PS mg/ml | Total Protein mg/ml | % Free PS |
|---|---|---|---|
| Men X-TT Purified Conjugate | 1.08 | 2.44 | 7.87 |

Example 3

Development of Monoclonal Antibodies Against Serogroup X of *Neisseria meningitidis*

Splenocytes isolated from mice immunized with Men X conjugate were fused with SP2/O cells (mouse myeloma cells). The fused cells were selected using HAT (Hypoxanthine Aminopterin Thymidine) medium. The supernatant of respective fused cells was screened to check the presence of anti-Men X antibody by in-house analytical methods like bead based assay and rate nephelometry. Limiting dilution of the positive clones were done. The single anti-Men X antibody secreting clone was propagated to 6 well plate. The clone was subjected to second limiting dilution. Anti-Men X antibody secreting clone was selected by bead based assay. Selected clone was further propagated to 2 Liters for production of Anti-Men X Mab. The produced MAb was purified using protein A resin by affinity chromatography.

Example 4

Characterization of In-House Developed Monoclonal Antibody Against Meningococcal Polysaccharide Serogroup X (MEN XLD2P1A12P1CP2D10)

TABLE 3

| Sr. No. | Tests | | Specifications | Result | Remark |
|---|---|---|---|---|---|
| 1 | Specificity of MAb | | | | |
| | | Bead Based assay | Reactive to Serogroup X of MenPs, <10% cross reactive to other MenPs[#] | Complies | Complies |
| | | Nephelometry | Reactive to Serogroup X of MenPs, <10% cross reactive to other MenPs[##] | Complies | Complies |
| 2. | Protein Concentration | | Report value (mg/ml) | 1.0 | Complies |
| 3. | Analysis of Antibody by SDS-PAGE | | | | |
| | | Reducing sample treatment | Two bands of heavy and light chain should be observed | Complies | Complies |

TABLE 3-continued

| Sr. No. | Tests | Specifications | Result | Remark |
|---|---|---|---|---|
| | Non-reducing sample treatment | Antibody band of approximately 150 KD should be observed | Complies | Complies |

Cross reactivity was checked against Meningococcal Capsular Polysaccharides from serogroup A, C, W, Y and X. Other antigens were Tetanus toxoid and CRM197.
Cross reactivity was checked against Meningococcal Capsular Polysaccharides from serogroup A, C, W, Y and X.

Example 5

Dilution of Antibodies

Capture antibody was commercially procured from BD Biosciences. The dilution for capture antibody was made from the stock and was optimized. Similar approach was utilized for dilution of in-house monoclonal antibodies i.e. binding antibody against A C W Y & X.

The dilution for polyclonal capture antibody was between 1:5000 to 1:15000 in carbonate buffer, pH 9.6. The dilution for detection monoclonal antibody was between 1:3000 to 1:10000 in PBS, pH 7.2. The dilution for secondary antibody (preferably HRP-Conjugate antibody) was between 1:5000 to 1:15000 in PBS, pH 7.2.

Example 6

Sample Preparation Pre-Sandwich ELISA

Sample in lyophilized form was resuspended in phosphate buffer saline (PBS) (pH 7.2) having 107 mM KCl followed by further dilution. Whereas for liquid samples, direct dilution with PBS (pH 7.2) having 107 mM KCl was carried out.

Three vials of vaccine were taken for testing. Each vial was resuspended into 1 mL PBS and mixed. Appropriate volume of sample was taken in test tube and desired volume of PBS was added to dilute the sample. Sample was serially diluted so that the optical density of sample would fall into the standard curve. Three dilution prepared from individual three vials were used to have sample in triplicate in the assay.

Example 7

Protocol for Sandwich ELISA
1. The immunoplates were coated by serogroup specific antiserum (Men A, C, Y, W & X). (Dilution is 1:5000 to 1:15000).
2. Said plates were incubated at a temperature between 30 to 40° C. for a duration of about 1 to 2 hour.
3. Immunoplates were washed for 3 to 5 times by wash buffer: WFI+0.05% Tween 20).
4. Blocking buffer containing Phosphate buffer saline, 2 to 7% FBS and 0.05% Tween 20 was added.
5. Mixture was subjected to incubation at a temperature between 30 to 40° C. for a duration of about 1 to 2 hours.
6. Immunoplates were washed for 3 to 5 times with wash buffer.
7. Serially diluted polyvalent (Pentavalent/Quadrivalent) sample and standard were added.
8. The mixture was incubated at a temperature between 30 to 40° C. for a duration of about 1 to 2 hours.
9. Immunoplates were washed for 3 to 5 times with wash buffer.
10. The detection antibody solutions (Monoclonal Antibodies: 1:3000 to 1:10000) were added.
11. The mixture was incubated at a temperature between 30 to 40° C. for a duration of about 1 to 2 hours.
12. Immunoplates were washed for 3 to 5 times with wash buffer.
13. Secondary antibody preferably HRP-Conjugate antibody (Dilution is 1:5000 to 1:15000) was added.
14. The mixture was incubated at a temperature between 30 to 40° C. for a duration of about 1 to 2 hours.
15. 100 µL substrate (TMB) was added in all the wells.
16. Mixture was incubated at RT for 15 to 30 minutes.
17. 100 µL 2 N Sulphuric acid was finally added.
18. OD was read at 450 nm wherein reference was 630 nm.

Example 8

Accuracy, Variation and Sensitivity of Novel Sandwich ELISA Method

TABLE 4

Accuracy study: Percentage Recovery (Refer FIGS. 1 to 5)

| Serogroup | Concentration in vaccine Vial µg/vial) | Spike (µg) | Expected Concentration (µg/vial) | Obtained Concentration (µg/vial) | Recovery (%) |
|---|---|---|---|---|---|
| X | 30.44 | 9.14 | 39.36 | 40.14 | 102 |
| A | 30.44 | 12.00 | 38.55 | 38.55 | 100 |
| C | 26.35 | 9.37 | 38.85 | 42.38 | 109 |
| Y | 33.10 | 13.63 | 51.90 | 51.48 | 99 |
| W | 27.21 | 11.40 | 37.90 | 38.12 | 101 |

Note:
All values for the assay in µg/Vial

TABLE 5

Figure 1:
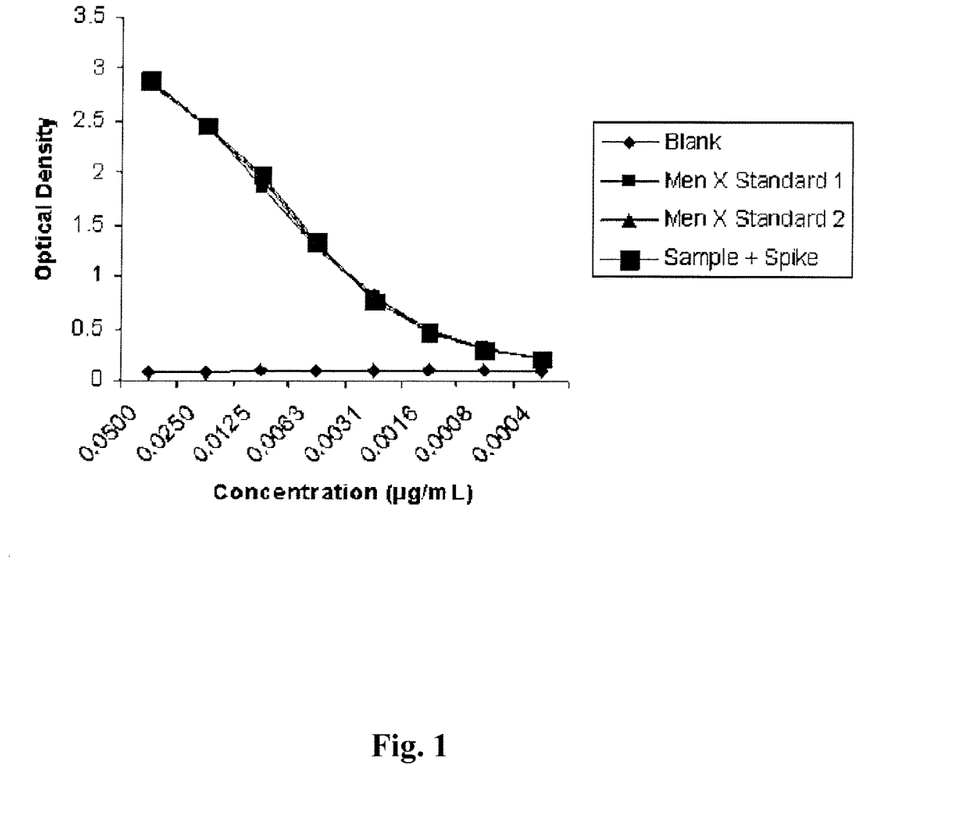
FIG. 1: Sandwich ELISA's accuracy study for Men X Serogroup.
Figure 2:
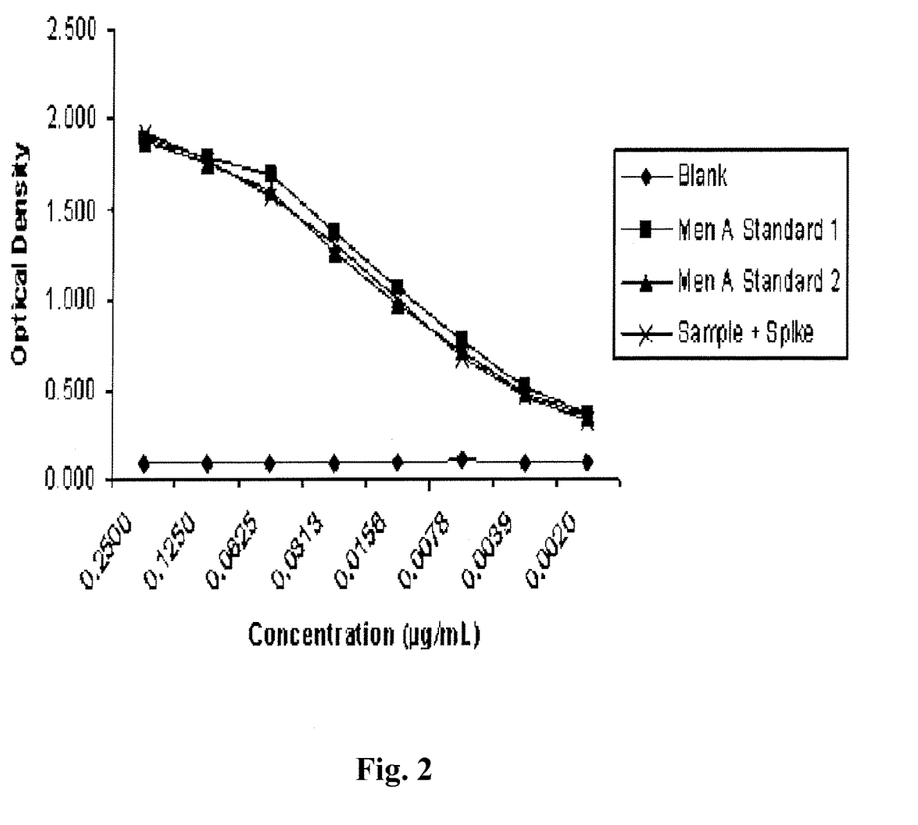
FIG. 2: Sandwich ELISA's accuracy study for Men A Serogroup.
Figure 3:
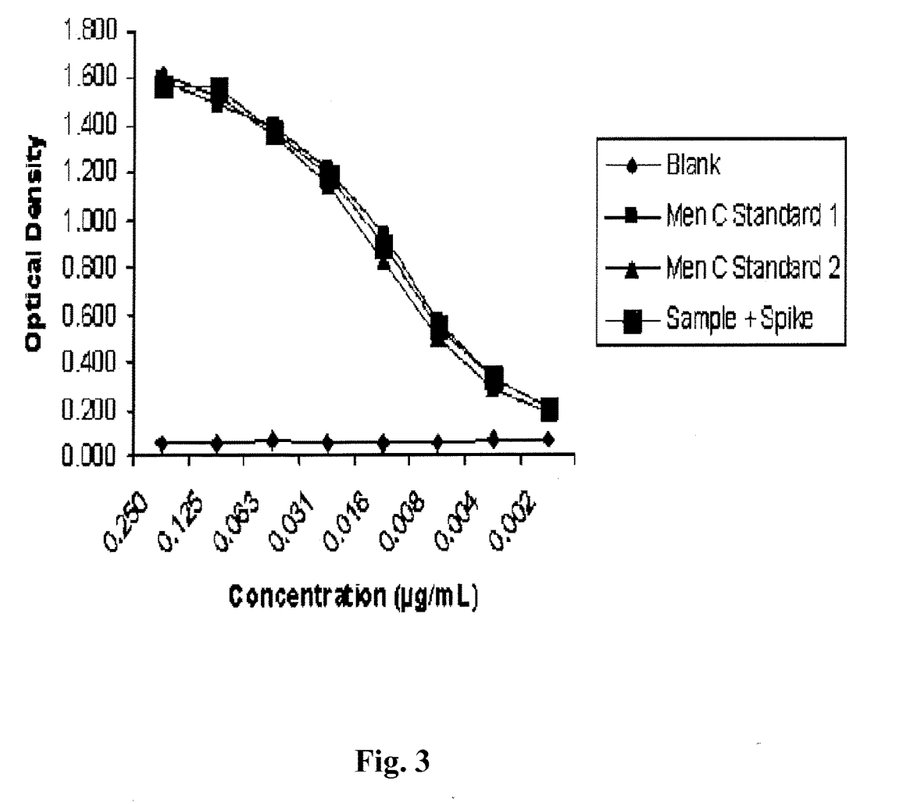
FIG. 3: Sandwich ELISA's accuracy study for Men C Serogroup.
Figure 4:
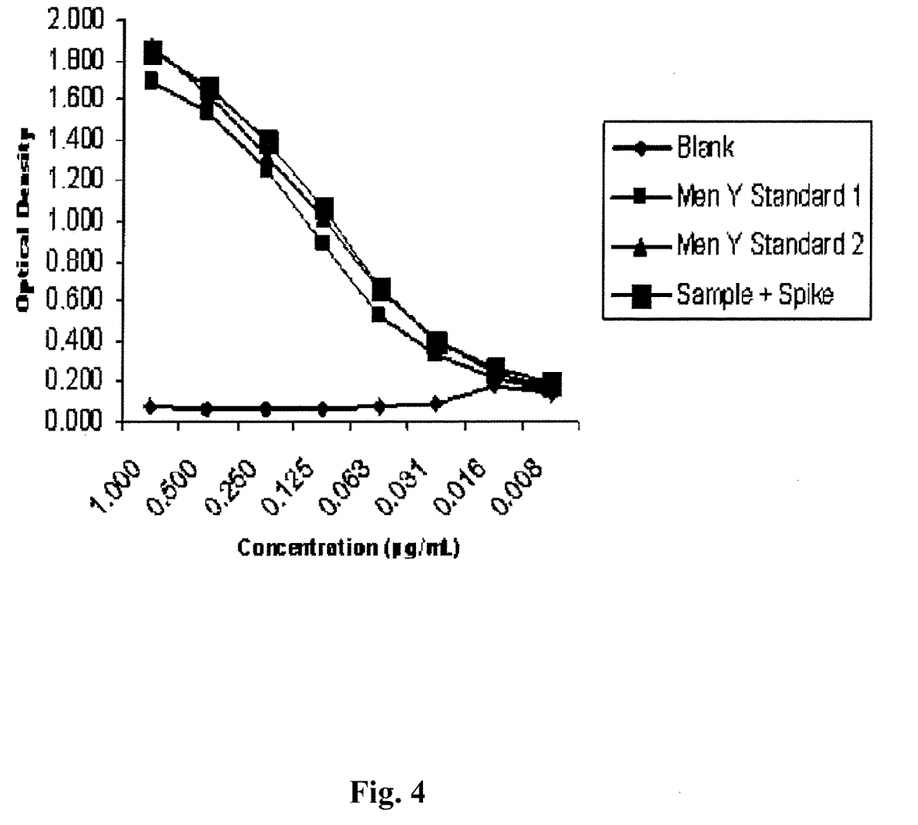
FIG. 4: Sandwich ELISA's accuracy study for Men Y Serogroup.
Figure 5:
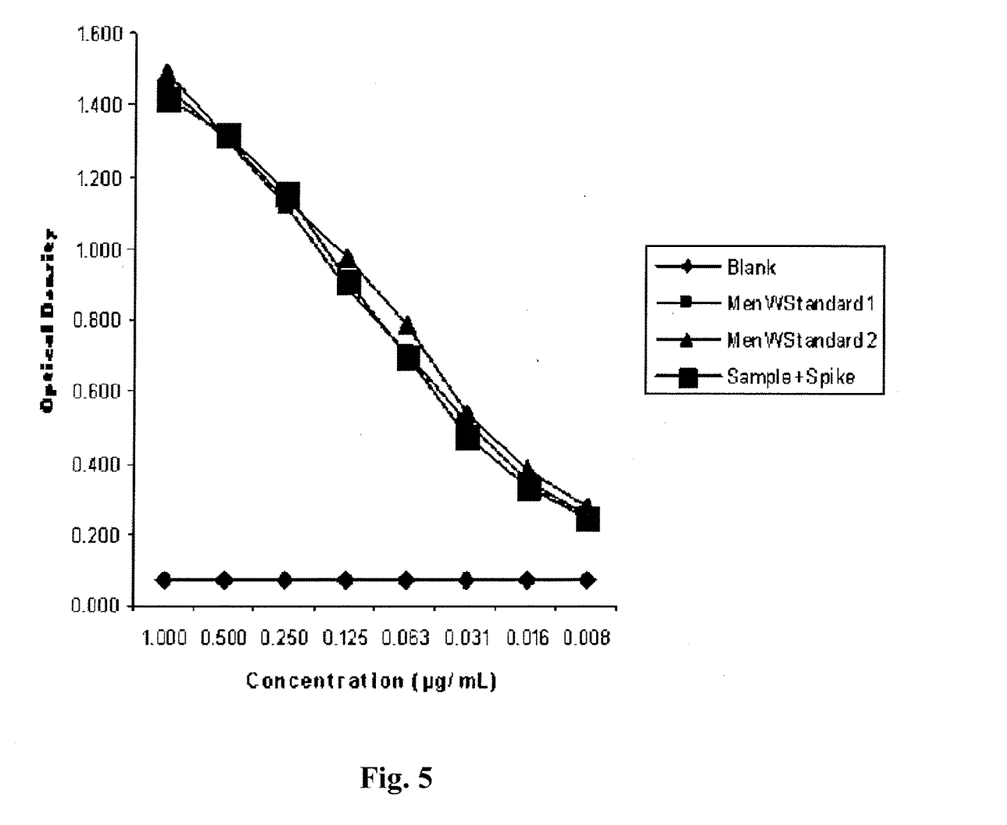
FIG. 5: Sandwich ELISA's accuracy study for Men W Serogroup.
Figure 6:
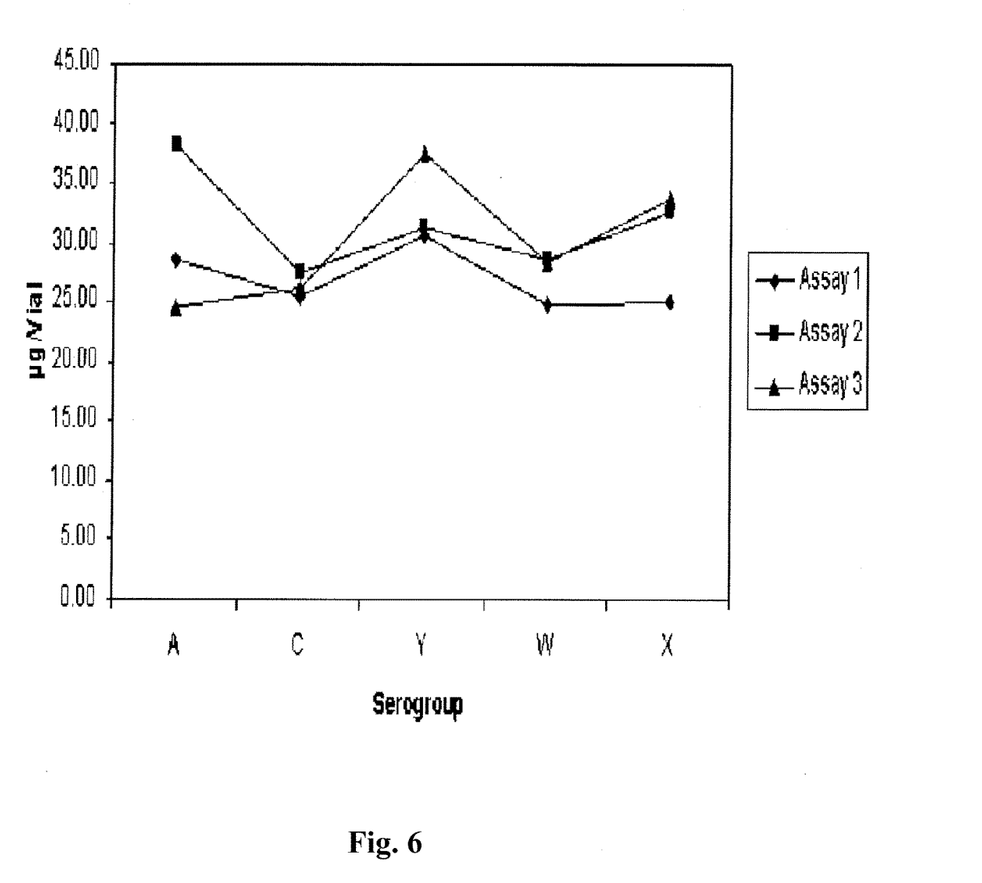
FIG. 6: Assay variation for Sandwich ELISA's for all serogroups Men X, A, C, Y and W.
Figure 7:
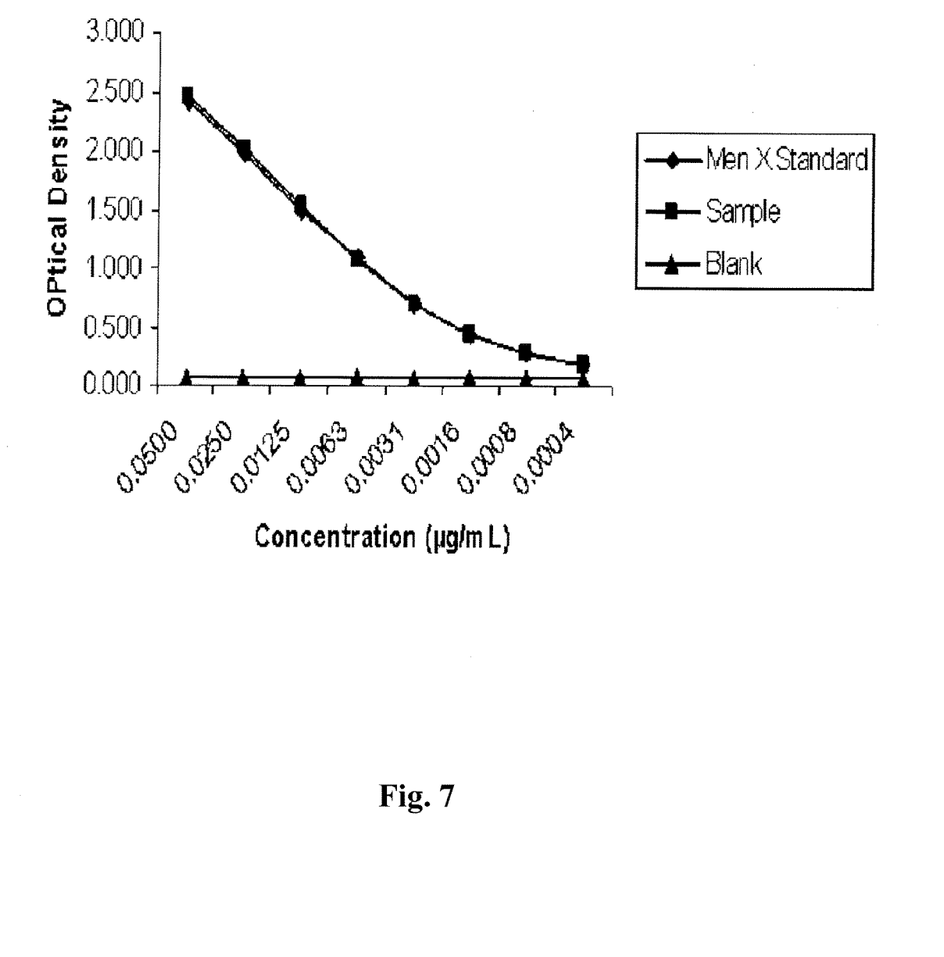
FIG. 7: Sandwich ELISA's Sensitivity study for Men X Serogroup.
Figure 8:
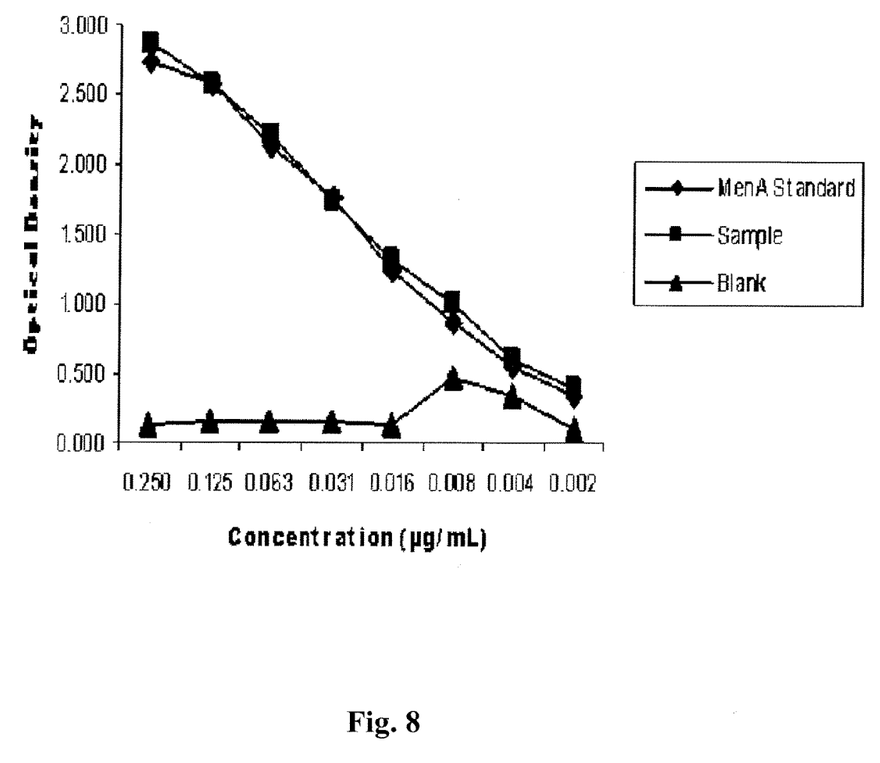
FIG. 8: Sandwich ELISA's Sensitivity study for Men A Serogroup.
Figure 9:
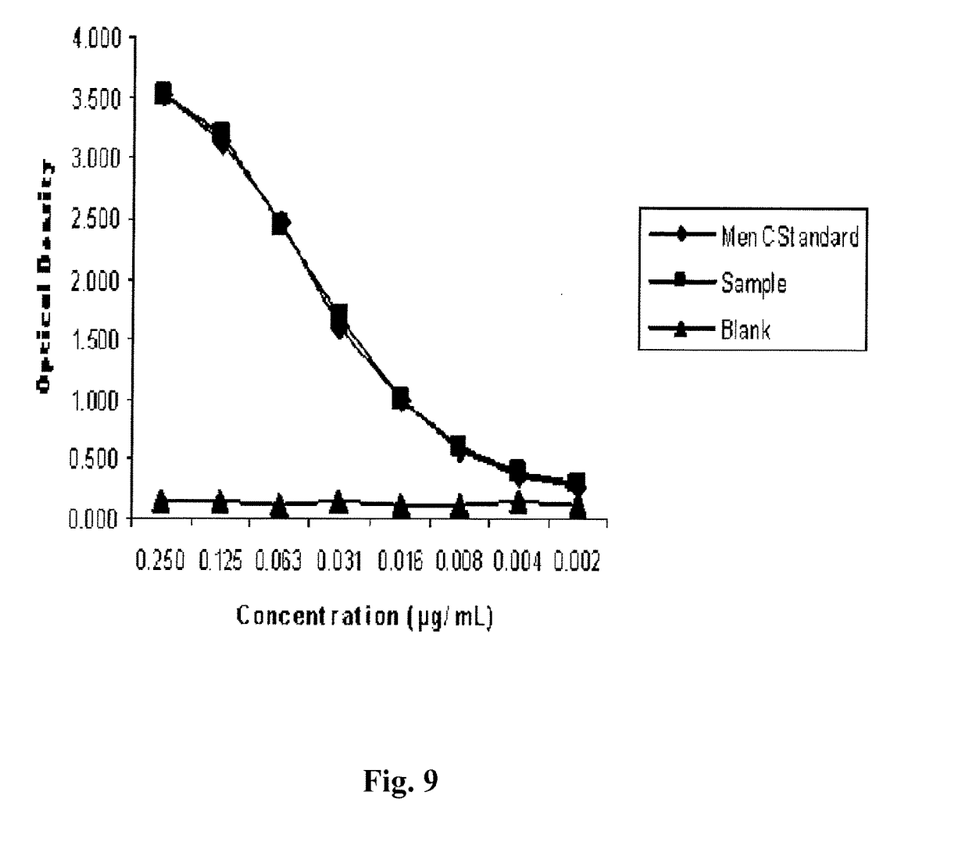
FIG. 9: Sandwich ELISA's Sensitivity study for Men C Serogroup.
Figure 10:
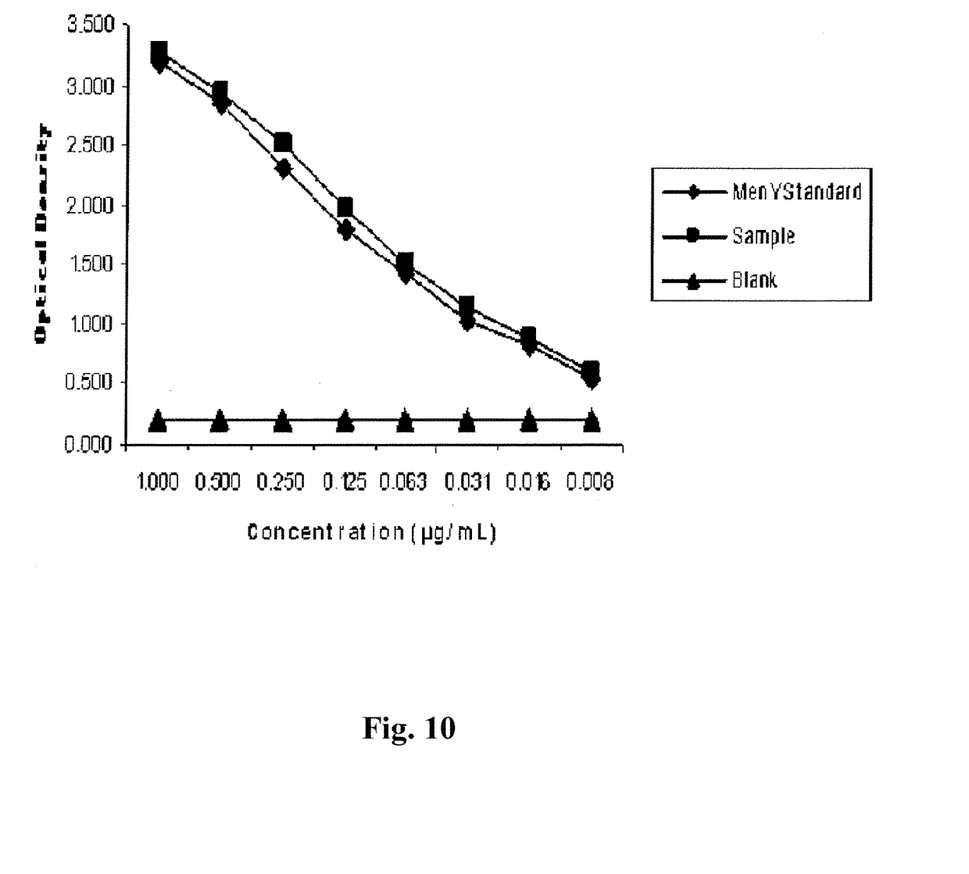
FIG. 10: Sandwich ELISA's Sensitivity study for Men Y Serogroup.
Figure 11:
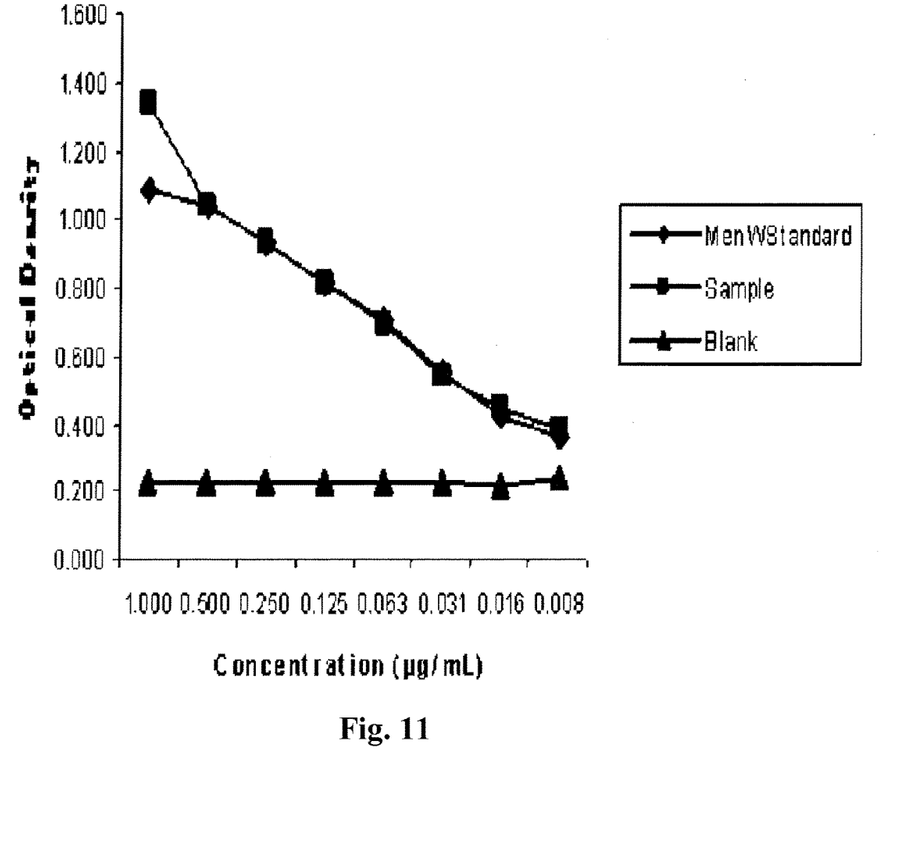
FIG. 11: Sandwich ELISA's Sensitivity study for Men W Serogroup.

Assay Variation(Refer FIG. 6)

| Serogroup | Assay 1 | Assay 2 | Assay 3 | Average | Standard Deviation | % Coefficient Variation |
|---|---|---|---|---|---|---|
| X | 24.98 | 32.48 | 33.79 | 30.42 | 4.75 | 15.63 |
| A | 28.58 | 38.19 | 24.16 | 30.46 | 6.98 | 22.92 |
| C | 25.42 | 27.59 | 26.10 | 26.37 | 1.11 | 4.21 |
| Y | 30.50 | 31.31 | 37.44 | 33.08 | 3.79 | 11.47 |
| W | 24.73 | 28.58 | 28.33 | 27.21 | 2.15 | 7.92 |

TABLE 6

Optical density details

| Serogroup | Average Optical Density of Blank | Average Optical Density of least standard | Average Optical sample last dilution | Concentration of least standard (µg/mL) |
|---|---|---|---|---|
| X | 0.071 | 0.191 | 0.178 | 0.0004 |
| A | 0.103 | 0.352 | 0.388 | 0.002 |
| C | 0 . . . 135 | 0.267 | 0.287 | 0.002 |
| Y | 0.201 | 0.543 | 0.609 | 0.008 |
| W | 0.234 | 0.359 | 0.386 | 0.008 |

The sensitivity of the assay was assessed based on the above data

TABLE 7

| Sensitivity (Refer FIGS. 7 to 11) | |
| --- | --- |
| Serogroup | Sensitivity of the method |
| X | 0.4 nanogram/mL |
| A | 2.0 nanograms/mL |
| C | 2.0 nanograms/mL |
| Y | 8.0 nanograms/mL |
| W | 8.0 nanograms/mL |

TABLE 8

| Limit of Detection (LOD) and Limit of Quantitation (LOQ) | | |
| --- | --- | --- |
| Serogroup | Limit of detection (LOD) | Limit of quantitation (LOQ) |
| X | 0.4 nanogram/mL | 1.6 nanogram/mL |
| A | 2.0 nanograms/mL | 8.0 nanograms/mL |
| C | 2.0 nanograms/mL | 8.0 nanograms/mL |
| Y | 8.0 nanograms/mL | 31 nanograms/mL |
| W | 8.0 nanograms/mL | 31 nanograms/mL |

Note:
The values obtained based on 4-Parametric curve analysis.
The quantitation range is selected in a linear region of the curve from the standard curve.

Said Sandwich ELISA of instant disclosure carried out using i) a novel monoclonal antibody against *N. meningitidis* serogroup X Polysaccharide, ii) specific dilutions of polyclonal capture antibody, detection monoclonal antibody and secondary antibody and iii) a prior sample treatment step, surprisingly showed a) optimal specificity, sensitivity for quantifying serogroup X polysaccharide in a multivalent ACWYX vaccine wherein LOD was 0.4 ng/ml and LOQ was 1.6 ng/ml for Men X b) did not show any interference due to excipient unlike the HPAEC-PAD and other chemical methods.

While exemplary embodiments are described above, it is not intended that these embodiments describe all possible forms of the disclosure. Rather, the words used in the specification are words of description rather than limitation, and it is understood that various changes may be made without departing from the spirit and scope of the disclosure.

What is claimed is:

1. A method for quantification of conjugated *N. meningitidis* serogroup X capsular polysaccharide in a sample using an immunological assay, the method comprising:
    providing a solid support coated with a capture polyclonal antibody;
    providing a sample including *N. meningitidis* serogroup X capsular polysaccharide-TT conjugate and unconjugated *N. meningtitidis* serogroup X capsular polysaccharide, wherein the sample is lyophilized and resuspended in phosphate buffer saline having pH 7.2±0.2 comprising KCl at a concentration from 75 mM to 140 mM followed by further dilution or the sample is liquid and directly diluted with phosphate buffer saline having pH 7.2±0.2 comprising KCl at a concentration from 75 mM to 140 mM;
    applying the sample to the solid support coated with capture polyclonal antibody;
    removing unbound sample;
    providing a detection monoclonal antibody;
    applying the detection monoclonal antibody to the solid support;
    removing unbound detection monoclonal antibody;
    applying labeled secondary antibody with a label; and
    detecting the label;
    wherein the assay does not show any interference due to presence of sucrose and glucose excipients.

2. The method according to claim 1, wherein the capture polyclonal antibody is obtained from rabbit antisera and the detection monoclonal antibody is obtained from fusion of mice splenocyte cells and mouse myeloma cells.

3. The method according to claim 1, wherein
    dilution of capture polyclonal capture antibody is between 1:5000 to 1:15000 in carbonate buffer, pH 9.6;
    dilution of the detection monoclonal antibody is between 1:3000 to 1:10000 in phosphate-buffered saline (PBS), pH 7.2; and
    dilution of the labeled secondary antibody is between 1:5000 to 1:15000 in phosphate-buffered saline (PBS), pH 7.2.

4. The method according to claim 1, wherein said detection monoclonal antibody does not show cross-reactivity with *N. meningitidis* serogroup polysaccharides A, C, W and Y.

5. The method according to claim 1, wherein limit of detection (LOD) is 0.4 ng/ml for *N. meningitidis* X.

6. The method according to claim 1, wherein the solid support is selected from the group consisting of polyvinyl chloride (PVC), polystyrene, agarose and sepharose.

7. The method according to claim 6, wherein the solid support is polystyrene.

8. The method according to claim 6, wherein the support is formed as a microtitration plate, tube or bead.

9. The method according to claim 8, wherein the microtitration plate is an activated immuno-assay plate.

10. The method according to claim 1, wherein the label is selected from the group consisting of an enzyme label, fluorescent label, a radioactive label and biotin.

11. The method according to claim 10, wherein the enzyme label is selected from the group consisting of a single enzyme, an oligomeric form of an enzyme, and an enzyme/antienzyme complex.

12. The method according to claim 11, wherein the enzyme label is coupled to an alternative detection system.

13. The method according to claim 11, wherein the enzyme label is selected from the group consisting of alkaline phosphatase, horse radish peroxidase, beta-galactosidase and urease.

14. The method according to claim 11, wherein the label enzyme is horse radish peroxidase.

15. The method according to claim 1, wherein the sample comprises a monovalent *N. meningitidis* serogroup X capsular polysaccharide.

16. The method according to claim 15, wherein the sample comprises at least one additional *N. meningitidis* serogroup capsular polysaccharide selected from the group consisting of *N. meningitidis* serogroup A, *N. meningitidis* serogroup C, *N. meningitidis* serogroup W and *N. meningitidis* serogroup Y.

17. The method according to claim 15, wherein the sample comprises at least one additional *N. meningitidis* serogroup capsular polysaccharide-protein conjugate selected from the group consisting of *N. meningitidis* serogroup A, *N. meningitidis* serogroup C, *N. meningitidis* serogroup W and *N. meningitidis* serogroup Y.

18. The method according to claim 1, wherein the sample comprises at least one non *N. meningitidis* antigen selected from the group consisting of *S. pneumoniae* and *H. influenzae*.

19. The method according to claim 1, wherein the sample includes *Neisseria meningitidis* X polysaccharide from *N. meningitidis* X8210 strain and tetanus toxoid protein.

\* \* \* \* \*